United States Patent [19]
Taniguchi et al.

[11] 3,931,348
[45] Jan. 6, 1976

[54] PROCESS FOR PREPARING DIMETHYL NAPHTHALENE

[75] Inventors: Katsuo Taniguchi, Iwakuni; Shizunori Miyamoto; Hideto Matsuoka, both of Ohtake, all of Japan

[73] Assignee: Mitsui Petrochemical Industries, Ltd., Tokyo, Japan

[22] Filed: Dec. 21, 1973

[21] Appl. No.: 427,342

[30] Foreign Application Priority Data
Dec. 25, 1972 Japan............................. 47-129386
Feb. 14, 1973 Japan............................. 48-18326

[52] U.S. Cl. ...... 260/668 F; 260/668 B; 260/668 D
[51] Int. Cl. ........................................... C07c 15/24
[58] Field of Search.......... 260/668 B, 668 F, 668 D

[56] References Cited
UNITED STATES PATENTS

| | | | |
|---|---|---|---|
| 2,958,643 | 11/1960 | Friedman.................... | 260/668 D |
| 3,244,758 | 4/1966 | Eberhardt.................... | 260/668 B |
| 3,775,498 | 11/1973 | Thompson.................... | 260/668 D |
| 3,781,375 | 12/1973 | Shima........................... | 260/668 D |

*Primary Examiner*—Veronica O'Keefe
*Attorney, Agent, or Firm*—Sherman & Shalloway

[57] ABSTRACT

A process for preparing dimethyl naphthalenes, which comprises heating a compound, such as methyl-4-(p-tolyl) butane, methyl-4-(p-tolyl)butene or methyl-4-(p-tolyl)butadiene, in the presence of a cyclization-dehydrogenation catalyst.

13 Claims, No Drawings

PROCESS FOR PREPARING DIMETHYL NAPHTHALENE

This invention relates to a process for preparing dimethyl napthalenes of high purity in a high yield by a one-step reaction starting from a compound of the formula (I)

   (I)

wherein R is a member selected from the group consisting of alkyl, alkylene and alkadiene groups each containing 5 carbon atoms and one pendant methyl group.

The dimethyl naphthalenes are suitable as starting materials for naphthalenedicarboxylic acids which are useful for producing polyesters having good crystallinity.

It has previously been known [J. Catalysis 3, 129 (1964)] that an alkylbenzene, for example propylbenzene, can by cyclized as shown in the following scheme by a dehydrocyclization reaction using a platinum supported alimina catalyst.

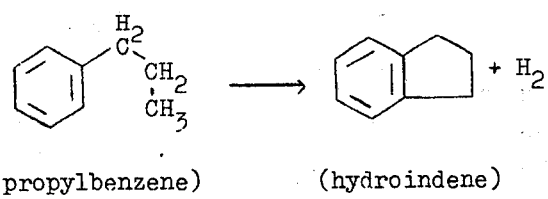

(propylbenzene)         (hydroindene)

This type of reaction is distinguished from the aromatization in the present invention in that the resultant ring is a saturated ring.

Such a type of reaction for producing dimethyl naphthalenes has been known, for example, from Japanese Laid-Open Publication No. 31962/72 laid open on Nov. 14, 1972 which discloses that dimethyl tetralin (or dimethyl tetrahydronaphthalene) of the formula

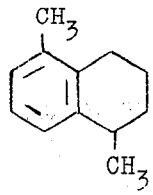 or 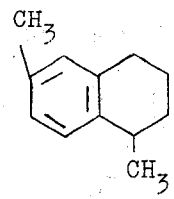

is prepared by dehydrocyclization of tolyl pentene or tolyl pentadiene of the formula

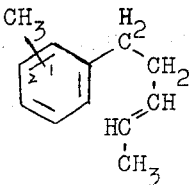

wherein the methyl group is at the 1- or 2-position of the benzene ring, using a solid acid catalyst sych as a solid phosphoric acid catalyst, a solid sulfuric acid catalyst, a silica-alumina catalyst or a zeolite catalyst; or from Japanese Laid-Open Publication No. 14154/72 laid open on Aug. 4, 1972 which discloses that 2,6-dimethyl naphthalene is prepared by dehydrogenation of the dimethyl tetralin obtained as above under conditions such as to induce both aromatization and isomerization.

It has been found that a catalyst (to be termed a "cyclization-dehydrogenation catalyst" in the sense that it can induce both cyclization and aromatization at the same time) exists which can give 1,6-, 2,6- or 2,7-dimethyl naphthalene at a good selectivity from the compound of formula (I) without relying on a two-step reaction comprising the formation of a saturated ring by dehydrocyclization and the aromatization of the saturated ring by dehydrogenation; and that the use of this special type of catalyst can produce the desired dimethyl naphthalene of high purity in a high yield directly from the compound of formula (I).

Accordingly, an object of this invention is to provide a process for preparing dimethyl naphthalenes, especially 1,6-, 2,6-, or 2,7-dimethyl naphthalene, of high purity in a high yield and at a good selectivity by a shortened reaction process.

Other objects and advantages of this invention will become more apparent from the following description.

The compound of the formula (I) used in the process of this invention is a known compound, and can be prepared, for example, by the following reactions.

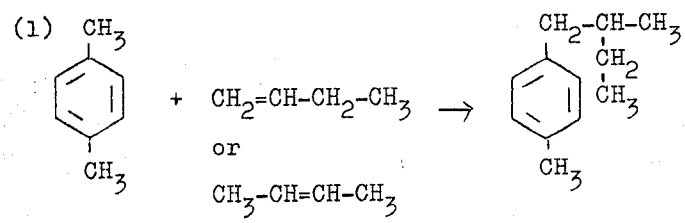

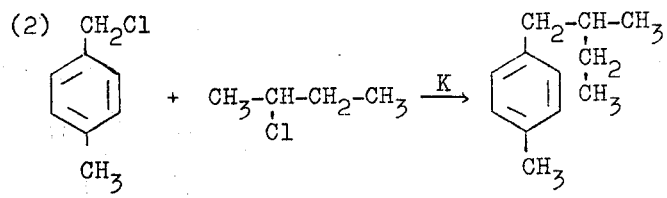

(3) 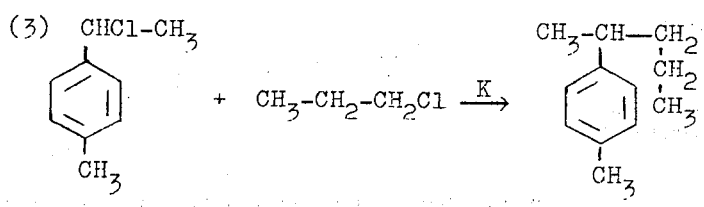
(4) 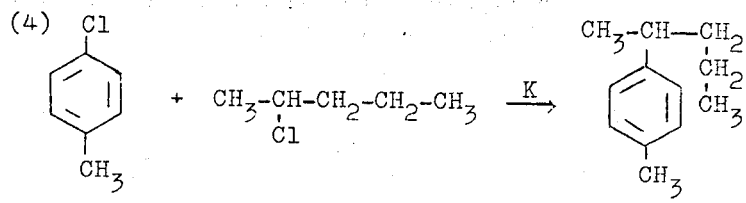
(5) 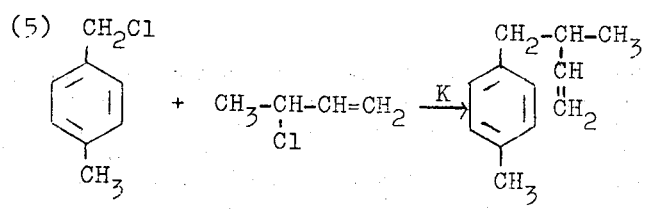
(6) 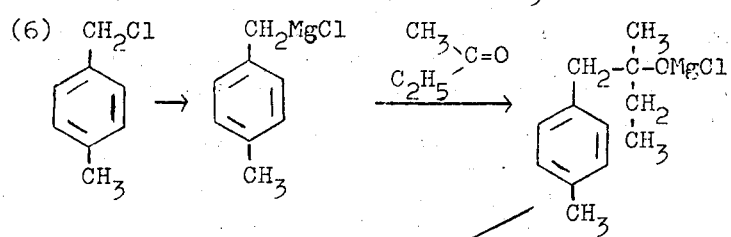
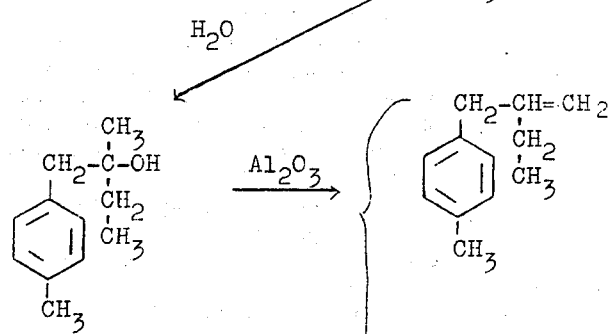
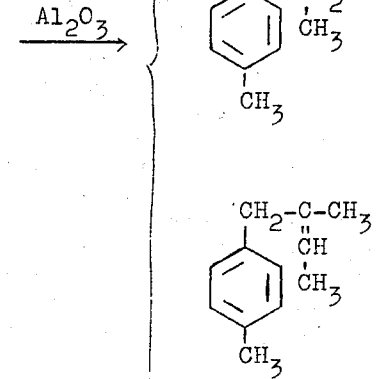
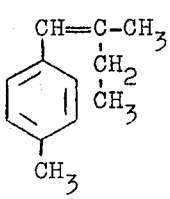
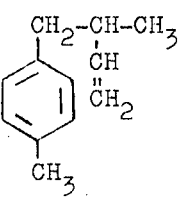

(7) 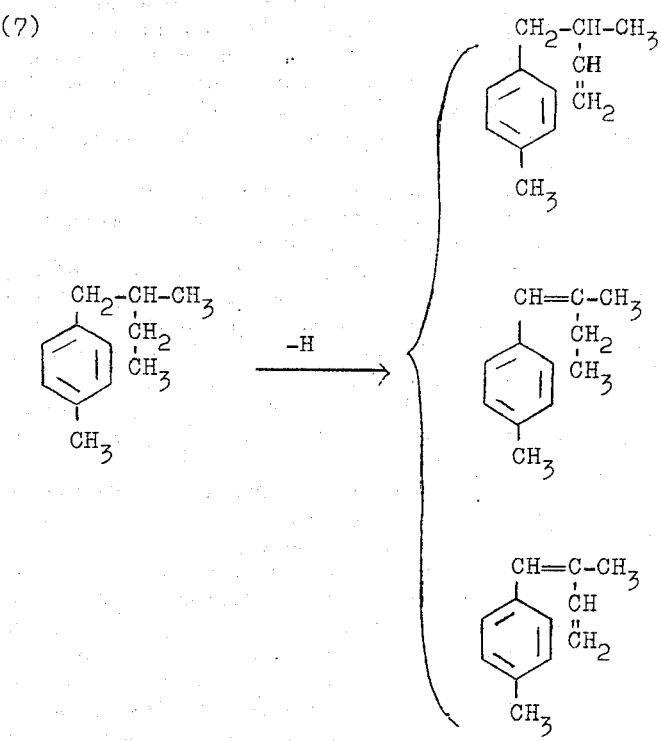
(8) 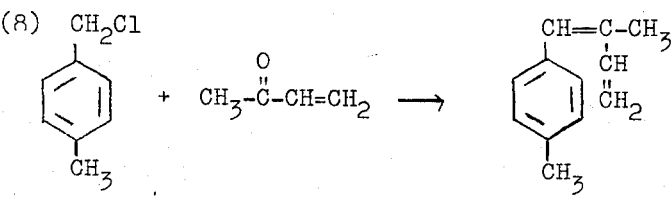
(9) 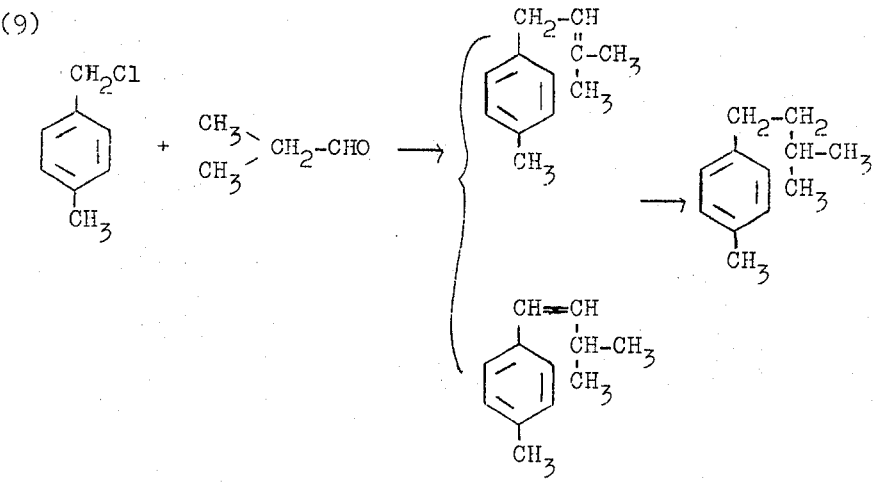
(10) 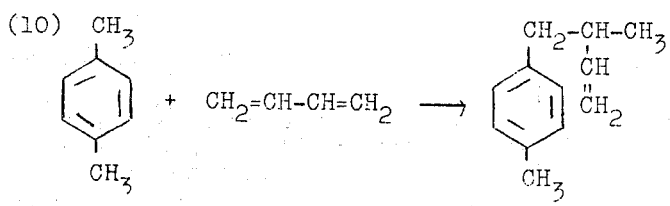

Preferably, the compound of the formula (I) is prepared by an addition between p-xylene and butene (butene-1, butene-2) or butadiene, as shown by the reactions (1) and (10) cited above.

It is known that when an olefin is added to an alkyl-substituted aromatic compound, the side chain of the compound is alkylated using a basic catalyst. For example, processes are known in which ethylene is added to o, m, or p-xylene, toluene or ethylbenzene using sodium-anthracene as a catalyst, or in which propylene, 1-butene, isobutene or 1-octene is added to toluene using sodium-anthracene or potassium as a catalyst and o-chlorotoluene as a promoter (J. A. C. S. Vol. 77, pages 554 to 559, and J. A. C. S. Vol. 78, pages 4316–4322).

However, there has been no literature reference which discloses the production of a side-chain alkylated product by the addition of butene and butadiene to p-xylene.

An alkali metal compound can be utilized as a catalyst for use in the addition-reaction between p-xylene and butene or butadiene. Suitable alkali metal compounds are, for example, $C_1$–$C_6$ alkyl compounds of alkali metals such as butyl lithium, butyl potassium, amyl sodium, or hexyl sodium; and $C_6$–$C_8$ aryl compounds of alkali metals such as phenyl potassium, phenyl sodium or phenyl lithium. Especially preferably, the use of a catalyst prepared by supporting an alkali metal such as sodium or potassium on a carrier can lead to a remarkable improvement of the reactivity between p-xylene and 1-butene and/or 2-butene, and of the selectivity of the reaction product, i.e., 3-methyl-4-(p-tolyl) butane.

Preferred alkali metals used as a catalyst component for the addition reaction are, for example, lithium, sodium, potassium, and rubidium, the last three being especially preferred. The carrier used for preparing the catalyst should be those having a relatively high surface area and a relatively low acidity. Those having a surface area of at least 2 m²/g and an acidity of at most pKa +1.5 are preferred. Specific examples of the carrier are graphite, magnesia, alumina, soda lime, potassium iodide, potassium carbonate, calcium carbonate and calcium sulfate. The graphite, alumina, soda lime and potassium carbonate are preferred. From the viewpoint of the active lifetime of the catalyst, the carrier is preferably in the finely divided form rather than in the form of coarse particles.

A suitable method for supporting the alkali metal on the carrier comprises adding the alkali metal in small portions with stirring at 200° to 250°C. in an atmosphere of an inert gas such as nitrogen, to a carrier calcined for several hours at a temperature of as high as several hundred degrees centigrade in an atmosphere of an inert gas such as nitrogen, and heating the mixture at this temperature with stirring for several minutes to several hours.

The addition reaction between p-xylene and butene and/or butadiene is generally effected by a method comprising mixing p-xylene with a catalyst, aging the mixture, bringing the aged mixture into contact with butene and/or butadiene, and heating them. It should be noted however that the invention is not limited to this specific method, but any other available methods can be used.

The aging of the mixture of the catalyst and p-xylene is carried out while the mixture is being thoroughly stirred in an atmosphere of an inert gas such as nitrogen or argon. The temperature at this time may be room temperature or higher. Then, the reaction product containing the catalyst is cooled, brought into contact with the butene and/or butadiene, and then heated to a temperature of ⅛° to 200°C. This results in the side-chain alkylation of butene and/or butadiene to p-xylene.

A diluent may be used for this addition reaction, and a saturated aliphatic hydrocarbon such as decane or dodecane is used as the diluent.

When a carrier-supported alkali metal is used as the catalyst in this addition reaction, the conversion and selectivity of the starting compound of the formula (I) become higher than in the case of using a carrier-free catalyst. Thus, the addition reaction can be performed under relatively mild conditions, and this makes it easy to separate the by-products or purify the compound of formula (I).

By the above process, methyl-4-(p-tolyl) butane, methyl-4-(p-tolyl) butene, or methyl-4-(p-tolyl)butadiene of the formula (I) can be obtained.

According to the process of this invention, the compound of formula (I) having one pendant methyl group is heated in the presence of the cyclization-dehydrogenation catalyst to perform both cyclization and aromatization concurrently. According to the position of the side-chain, the compound is converted to 1,6-, 2,6-, or 2,7-dimethyl naphthalene, as shown by the following formula in which the unsaturated bond and hydrogen atoms corresponding to R in formula (I) are omitted.

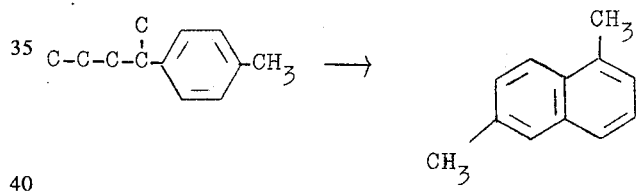

(1,6-dimethyl naphthalene)

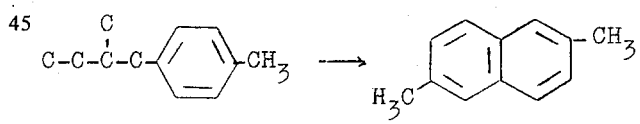

(2,6-dimethyl naphthalene)

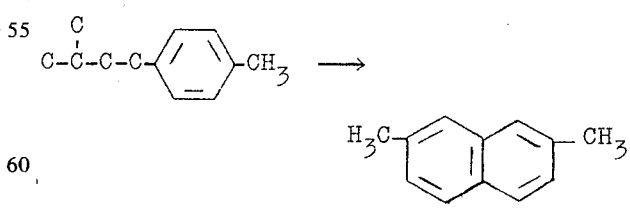

(2,7-dimethyl naphthalene)

Of the compounds having the formula (I), methyl-4-(p-tolyl) butene and methyl-4-(p-tolyl) butadiene having a double bond at the butane skeleton are desirable starting materials since they give rise to a remarkable increase in conversion and yield. The double bond in the methyl-4-(p-tolyl) butene may be located at any desired position. However, when a methyl tolyl butane having a butane skeleton at a position other than the terminal positions, such as methyl-3-(p-tolyl) butane or a methyl tolyl butane having a m-tolyl or o-tolyl group instead of the p-tolyl group is used as a starting material, isomers other than the desired 1,6-, 2,6- and 2,7-dimethyl naphthalenes are produced in large quantities, and it is impossible to produce 1,6-, 2,6- or 2,7-dimethyl naphthalene selectively. Accordingly, the starting material used in this invention is a compound of the following formula (I)

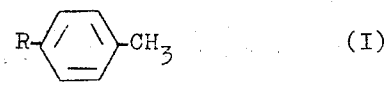

wherein R is a member selected from the group consisting of alkyl, alkylene and alkadiene groups each containing 5 carbon atoms and one pendant methyl group, in which the p-tolyl group is substituted at the terminal position of the butane skeleton.

In the process of this invention, the reaction is preferably carried out by the vapor-phase catalytic reaction procedure. The reaction temperature is preferably about 200 to about 700°C., more preferably about 300° to about 600°C. Contact for about 0.1 second to about 15 seconds, preferably about 0.1 second to about 10 seconds, more preferably about 3 seconds is sufficient to about 8 seconds. The catalyst layer in the vapor-phase catalytic reaction may either be of a fixed-bed type or a fluidized-bed type. In the performance of the vapor phase catalytic reaction, the compound of formula (I) is vaporized by an evaporator through or not through a pre-heater, and fed into the catalyst layer where it is brought into contact with the catalyst layer. At this time, a suitable diluent or carrier gas can be utilized. Such a gas may be an inert gas such as nitrogen gas, argon gas or steam, and also an aromatic hydrocarbon such as benzene or toluene, an alicyclic hydrocarbon such as cyclohexane, and an aliphatic hydrocarbon such as heptane or hexane in vapor form.

Specific examples of the cyclization-dehydrogenation catalyst suitable for use in the process of this invention are oxides of chromium, rhenium or a mixture of these. The catalyst can be used as supported on a suitable solid carrier. Examples of such a carrier are silica, alumina, magnesia, boria, thoria, titania, and mixtures of at least two of these with one another. Furthermore, an oxide of a metal selected from the group consisting of alkali metals and alkaline earth metals can be used as a promoter together with the catalyst. Specific examples of the promoter are oxides of metals selected from the group consisting of lithium, sodium, potassium, cesium, magnesium, calcium, stronitium, barium, and mixtures of at least two of these with one another.

In the present invention, the amount of the catalyst used is not particularly limited, but can be varied over a wide range. Usually, the amount of the catalyst is at least 0.001 mol, such as 0.001 mol to 1 mol, preferably about 0.005 to about 0.5 mol, per mol of the compound of the formula (I). The amount of the promotor to be used is preferably about 0.1 to about 20% by weight based on the weight of the catalyst. If the selectivity to 2,6-dimethyl naphthalene is of special concern, the promotor is used preferably in an amount of about 1 to about 8% by weight. The amount of the carrier is not restricted in particular, but preferably, it is used in an amount such that the amount of the chromium and/or rhenium oxide used as a catalyst is about 0.5 to about 10% by weight calculated as metal based on the weight of the solid carrier.

In the commercial performance of the process of this invention, the use of a carrier is preferred. The use of a promotor is beneficial in that it leads to a further increase in the selectivity of forming the desired dimethyl naphthalene, and serves to inhibit the formation of by-products such as dimethyl naphthalene isomers other than 1,6-, 2,6-, and 2,7-dimethyl naphthalenes to a greater extent.

The catalyst supported on a carrier together, if desired, with a promoter can be prepared by various known methods, such as a method wherein the carrier is impregnated with a chromium and/or rhenium compound by a suitable means, followed by drying and calcining; a method wherein the carrier and the above compound are co-gelled, dried and calcined; a precipitation method; a method in which a chromium and/or rhenium compound is supported on the carrier by sublimation, followed by pyrolysis; a method in which a solution prepared by adding water to a water-soluble compound of chromium or rhenium is added to a solid carrier to impregnate the solution therein and they are heated and calcined by passing clean air; a method wherein a solid carrier such as γ-alumina is well shaken in an excess of an acid containing chromium or rhenium, allowed to stand, and after removal of the liquid, dried and reduced with hydrogen; a method wherein a solid catalyst is immersed in a solution of a chromium or rhenium compound, dried, calcined, and reduced; a method wherein gels are prepared separately from a carrier-forming compound such as aluminum nitrate and a catalyst-forming compound such as chromium nitrate, and then mixed with each other; a method wherein a mixed solution of a carrier-forming compound such as aluminum nitrate and a catalyst-forming compound such as chromium nitrate is poured into aqueous ammonia while maintaining the pH at not less than 8 and the product coprecipitated is dried and then calcined; a method wherein a solid carrier is immersed in an aqueous solution of a chromium or rhenium compound, dried, and then calcinated; a method wherein aluminum hydroxide is dissolved in an aqueous solution of sodium hydroxide, the solution is neutralized with nitric acid to a pH of 5.5 to 6.5, and the resultant precipitate is washed, after which potassium hydroxide, a small amount of nitric acid and a chromium or rhenium compound are added to the resultant gel, and they are kneaded, molded, and calcined; a method wherein small amounts of water, ammonium nitrate and a chromium or rhenium compound are added to aluminum hydroxide, and the resulting mixture is heat-treated, calcined, cooled, molded, and calcined in a stream of air; a method which comprises immersing a chromia-alumina catalyst in an aqueous solution of sodium hydroxide, and drying it, and preferably in a hydrogen atmosphere; a method which comprises immersing alumina calcined for long periods of time at a temperature of at least 700°C., in an aqueous solution of a hydroxide, halide, nitrate, sulfate or acetate of an alkali metal or alkaline earth metal for more than 20 hours, withdrawing it from the aqueous solution, drying and calcining the alumina for about 3 hours at a temperature of about 500°C. in air, thereby to form modified alumina having supported thereon the alkali metal or alkaline earth metal, then immersing the modified alumina in a solution of ammonium perrhenate in water or a perrhenic acid solution obtained by dissolving metallic rhenium in nitric acid or aqua regia having oxidizability, withdrawing the alumina from the solution, drying it, and then calcining it in nitrogen at a temperature of about 500° to 800°C.; a method similar to the above method except that calcination is carried out in an atmosphere of a reducing gas such as hydrogen or $H_2S$ instead of the nitrogen; or a method wherein the above modified alumina is finely divided, and ammonium perrhenate is sublimed and supported on the alumina, followed by pyrolysis.

The following Examples illustrate the present invention in greater detail.

REFERENTIAL EXAMPLE 1

γ-Alumina having a particle size of 150 to 200 mesh was calcined in nitrogen at 500° to 600°C. for 2.5 hours, and placed in a stirrer-equipped catalyst preparing device purged with argon. The device was heated to 200° to 250°C., and with stirring, a potassium was added in small portions. After adding all of the potassium, stirring was continued for about 1 hour at 200° to 250°C. to form a catalyst in which 5% by weight of potassium was supported on γ-alumina.

9.3 g. of this catalyst was taken into an ampoule purged with argon, and 161 mmols of p-xylene treated with sodium was added. The mixture was stirred at room temperature for some time, and aged. The aged mixture was replaced in a 100 cc rotary-stirring-type stainless steel autoclave purged with argon, and cooled with dry ice-methanol. 1-Butene and/or 2-butene treated with a molecular sieve was introduced in the amounts shown in Table 1. The autoclave was heated at 150°C. for the periods of time shown in Table 1, and cooled to room temperature to expel the unreacted 1-butene and/or 2-butene. A sample was taken from the residual liquid, and the composition of the reaction product was analyzed by gas-chromatography, and the selectivity (%) of 3-methyl-4-(p-tolyl) butane and the conversion (%) based on p-xylene were calculated. The results are shown in the following table.

Table 1

| Butenes (mmols) | Reaction time (hours) | Conversion (%) | Selectivity (%) |
|---|---|---|---|
| 1-butene (160) | 17.0 | 23.0 | 87.4 |
| 2-butene (155) | 3.0 | 12.2 | 87.1 |
| 1-butene (100) | | | |
| 2-butene (50) | 4.5 | 15.2 | 88.3 |

REFERENTIAL EXAMPLE 2

To 162 mmols of p-xylene were added 7 mmols of n-butyl lithium and 9 mmols of N,N,N',N'-tetramethylethylenediamine, and the mixture was stirred at room temperature for 2 hours, whereupon it turned brilliant orange. The resulting product was placed in an autoclave, and at the same time, 143 mmols of 1-butene was introduced into it. When they were reacted at 80° to 100°C. at an initial pressure of 15 Kg/cm², the pressure of the inside of the autoclave decreased gradually. After reacting for 5 hours, 3-methyl-4-(p-tolyl) butane was obtained in a selectivity of about 90%. This compound was distilled under reduced pressure to purity it. The resulting product was used in the following Examples.

REFERENTIAL EXAMPLE 3

0.05 Mol of p-methyl benzyl chloride and 0.05 mol of sec.-butyl chloride were dissolved in 100 ml. of toluene. The solution obtained was added dropwise to a toluene solution containing 0.1 mol of potassium metal with thorough stirring while obtaining the temperature of the solution at 20° to 30°C. After the addition, the temperature of the solution was raised to 50°C. with thorough stirring to complete the reaction. After the reaction, the product became black violet, and a white powder was precipitated. The resultant product containing the unreacted matter and by-products was distilled to afford 3-methyl-4-(p-tolyl) butane. The resulting product was used in the following Examples.

REFERENTIAL EXAMPLE 4

A Grignard reagent of the formula

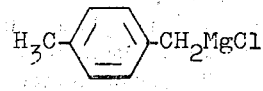

was obtained from 0.77 mol of metallic magnesium and 0.59 mol of p-methyl benzyl chloride. To this was added 0.6 mol of an ether solution of methyl ethyl ketone. After thorough reaction, a large excess of water was added to hydrolyze the reaction product. The resulting 3-methyl-4-(p-tolyl)-3-butanol was passed through a reaction tube packed with active alumina at 200° to 300°C. to afford the desired 3-methyl-4-(p-tolyl) butene almost quantitatively.

REFERENTIAL EXAMPLE 5

γ-Alumina was calcined in an atmosphere of nitrogen at 500°C. for about 5 hours, and transferred to a stirrer-equipped catalyst preparing device purged with argon. It was heated to 200° to 250°C., and with thorough stirring, metallic potassium was poured in small portions and dispersed and supported on the alumina. There was thus obtained a catalyst composed of γ-alumina on which 5% by weight of potassium was carried.

7 g of this catalyst was packed into a quartz reaction tube having an inside diameter of 15 mm in a current of argon. The reaction temperature was maintained at 170°C., and a gaseous mixture consisting of p-xylene, butadiene, n-heptane as a diluent, and nitrogen gas in a molar ratio of 1:5:10:5 was passed through the catalyst layer. The contact time of p-xylene was 24 seconds. The conversion of p-xylene was 43%, and the intended 3-methyl-4-(p-tolyl) butene was obtained in a yield of 8%.

EXAMPLE 1

Active alumina was immersed for one day in a stoichiometric amount of an aqueous solution of chromium nitrate, dried, and calcined in an atmosphere of nitrogen for 5 hours at 700°C. to form a chromia-alumina catalyst. 10 cc of this catalyst was packed into a quartz tube having an inside diameter of 15 mm, and maintained at 500°C. A gaseous mixture of 3-methyl-4-(p-tolyl) butane, benzene and nitrogen gas in a molar ratio of 1:3:8 was passed through this catalyst layer at normal atmospheric pressure. The contact time was 6 seconds. The composition of the catalyst, the conversion of 3-methyl-4-(p-tolyl) butane, the selectivity of the dimethyl naphthalene mixture and the proportions of the isomers of dimethyl naphthalane are shown in Table 2.

EXAMPLE 2

The chromia-alumina catalyst used in Example 1 was further immersed in an aqueous solution of sodium hydroxide, dried, and then calcined in an atmosphere of nitrogen at 700°C. for 5 hours to prepare a modified chromia-alumina catalyst. Using this catalyst, the cyclization dehydrogenation of 3-methyl-4-(p-tolyl) butane was performed in quite the same way as in Example 1.

The composition of the catalyst, the conversion of 3-methyl-4-(p-tolyl) butane, the selectivity of the dimethyl naphthalene mixture and the proportions of the isomers of dimethyl naphthalene are shown in Table 2.

EXAMPLE 3

The procedure of Example 2 was repeated except that the amount of sodium to be included in the catalyst was increased, the secondary calcination was performed in an atmosphere of hydrogen at 600°C. for 3 hours to cyclodehydrogenate 3-methyl-4-(p-tolyl) butane. The composition of the catalyst, the conversion of 3-methyl-4-(p-tolyl) butane, the selectivity of the dimethyl naphthalene mixture and the proportions of the isomers of dimethyl naphthalene are shown in Table 2.

EXAMPLE 4

Active alumina immersed in an aqueous solution of chromium nitrate was calcined, then immersed in an aqueous solution of lithium hydroxide, and calcined in an atmosphere of hydrogen at 600°C. for 3 hours to form a modified chromia-alumina catalyst. Using this catalyst, the cyclization-dehydrogenation of 3-methyl-4-(p-tolyl) butane was carried out in quite the same way as in Example 1. The composition of the catalyst, the conversion of 3-methyl-4-(p-tolyl) butane, the selectivity of the dimethyl naphthalene mixture and the proportions of the isomers of dimethyl naphthalene are shown in Table 2.

EXAMPLE 5

Active alumina was immersed for one day in a stoichiometric amount of an aqueous solution of chromium nitrate, withdrawn, dried, and calcined in an atmosphere of nitrogen at 700°C. for 5 hours to form a chromia-alumina catalyst. This catalyst was further immersed in an aqueous solution of potassium hydroxide, withdrawn, dried, and calcined in an atmosphere of hydrogen at 600°C. for 3 hours to form a modified chromia-alumina catalyst.

Using this catalyst, the cyclization-dehydrogenation of 3-methyl-4-(p-tolyl) butane was carried out in quite the same way as in Example 1. The composition of the catalyst, the conversion of 3-methyl-4-(p-tolyl) butane, the selectivity of the dimethyl naphthalene mixture and the proportions of the isomers of the dimethyl naphthanlene are shown in Table 2.

EXAMPLE 6

20 g of reagent-grade chromium nitrate [$Cr(NO_3)_3.9H_2O$] and 375 g of aluminum nitrate [$Al(NO_3)_3.9H_2O$] were dissolved in 500 ml. of pure water. On the other hand, 150 g. of sodium carbonate ($Na_2CO_3$) was dissolved in 500 ml. of pure water. This solution was mixed with the first-prepared mixed aqueous solution of chromium nitrate and aluminum nitrate with thorough stirring at about 70°C. The resulting gel was thoroughly washed with water, and dried at 80°C. for 30 hours. It was further calcined in a stream of air at 700°C. for 5 hours to form a chromia-alumina catalyst which contained chromium in an amount of 6.7% by weight as $Cr_2O_3$.

The catalyst obtained was immersed in about 200 ml. of an aqueous solution containing 10 g. of calcium nitrare [$Ca(No_3)_2.4H_2O$], and after one day, dried and again calcined in air at 700°C. for 3 hours.

Using the catalyst so prepared, the cyclization-dehydrogenation of 3-methyl-4-(p-tolyl) butane was performed in the same way as in Example 1. The results are shown in Table 2.

EXAMPLE 7

Commercially available granular silica gel was immersed for one day in a calculated amount of an aqueous solution of chromium nitrate, dried, and calcined in an atmosphere of nitrogen at 700°C. for 5 hours. The catalyst consisted of 4.0% by weight of chromia and 96.0% by weight of silica.

Using this catalyst, the cyclization-dehydrogenation of 3-methyl-4-(p-tolyl) butane was performed in the same way as in Example 1. The results are shown in Table 2.

EXAMPLE 8

Silica-alumina containing 25% of alumina was immersed for about 50 hours in a 8% by weight aqueous solution of potassium hydroxide, and then calcined at 700°C. for 3hours. The resulting potassium-poisoned silica-alumina contained 2.3% by weight of potassium as $K_2O$. Chromium oxide was carried on it in the same way as in Example 1. The resulting catalyst consisting of 6.2% by weight of $Cr_2O_3$, 2.1% by weight of $K_2O$, 21.0% by weight of $Al_2O_3$, and 70.7% by weight of $SiO_2$.

Using this catalyst, the cyclization-dehydration of 3-methyl-4-(p-tolyl) butane was performed in the same way as in Example 1. The results are shown in Table 2.

Table 2

| Examples | | 1 | 2 | 3 | 4 | 5 | 6 | 7 | 8 |
| --- | --- | --- | --- | --- | --- | --- | --- | --- | --- |
| Composition of the cyclization-dehydrogenation catalyst (wt %) | Chromia | 3.4 | 6.1 | 5.8 | 6.1 | 5.8 | 6.5 | 4.0 | 6.2 |
| | Alumina | 96.6 | 93.0 | 90.2 | 92.1 | 90.7 | 91.5 | 0 | 21.0 |
| | Silica | 0 | 0 | 0 | 0 | 0 | 0 | 96.0 | 70.7 |
| | Alkali or alkaline earth metal oxide | 0 | Na* 0.9 | Na* 4.0 | Li* 1.8 | K* 3.5 | Ca* 2.0 | 0 | K* 2.1 |
| Conversion (%) | | 36.7 | 34.5 | 42.4 | 51.7 | 45.3 | 43.2 | 30.7 | 35.7 |
| Selectivity (%) of dimethyl naphthylene | | 24.9 | 33.2 | 61.1 | 56.8 | 57.2 | 63.2 | 20.6 | 30.6 |

Table 2-continued

| Examples | 1 | 2 | 3 | 4 | 5 | 6 | 7 | 8 |
|---|---|---|---|---|---|---|---|---|
| Proportions of the isomers of dimethyl naphthalene (%) | | | | | | | | |
| 2,6-dimethyl naphthalene | 70.7 | 87.5 | 94.3 | 90.9 | 90.7 | 94.0 | 63.6 | 96.2 |
| 2,7-dimethyl naphthalene | 12.5 | 6.8 | 4.1 | 5.0 | 5.0 | 4.1 | | 3.1 |
| 1,6-dimethyl naphthalene | 2.5 | 1.8 | 0.4 | 0.6 | 1.9 | 0.5 | | 0.6 |
| 1,4-dimethyl naphthalene | 0.7 | 0.5 | 0.1 | trace | | 0.6 | 36.4 | trace |
| 2,3-dimethyl naphthalene | 7.9 | 1.1 | 0.5 | 1.4 | 2.4 | 0.3 | | trace |
| Others | 5.7 | 2.3 | 0.7 | 2.1 | | 0.5 | | 0.1 |

*Na, Li, K, and Ca respectively show an oxide of sodium an oxide of lithium, an oxide of potassium, and an oxide of calcium.

EXAMPLE 9

Using the catalyst obtained in Example 3, a mixture of 80% of 2-methyl-4-(p-tolyl)-2-butene and 20% of 2-methyl-4-(p-tolyl)-3-butene was cyclodehydrogenated in the same way as in Example 1. The results are shown in Table 3.

EXAMPLE 10

Using the catalyst obtained in Example 3, 3-methyl-4-(p-tolyl)-2-butene was cyclodehydrogenated in the same way as in Example 1. The results are shown in Table 3.

EXAMPLE 11

Using the catalyst obtained in Example 3, a mixture consisting of 25% of 3-methyl-4-(p-tolyl)-2-butene and 75% of 3-methyl-4-(p-tolyl)-3-butene was cyclohydrogenated. The results are shown in Table 3.

EXAMPLE 12

Using the catalyst obtained in Example 3, a mixture consisting of 30% of 4-methyl-(p-tolyl)-2-butene and 70% of 4-methyl-4-(p-tolyl)-3-butene was cyclodehydrogenated in the same way as in Example 1. The results are shown in Table 3.

EXAMPLE 13

Using the catalyst obtained in Example 3, 3-methyl-4-(p-tolyl) butadiene was cyclodehydrogenated in the same way as in Example 1 except that the heating temperature was changed to 370°C. The results are shown in Table 3.

EXAMPLES 14 and 15

Commercially available active alumina was immersed for about 20 hours in a stoichiometric amount of an aqueous solution of potassium nitrate or calcium nitrate, withdrawn, dried, and calcined in air of 700°C. for 5 hours to form a potassium or calcium-supported alumina catalyst. The catalyst was further immersed in an aqueous solution of ammonium perrhenate, allowed to stand for 20 hours, withdrawn, dried, and dried, and calcined in an atmosphere of nitrogen at 700°C. for 3 hours, followed by further calcination of the calcined product in an atmosphere of hydrogen for about 1 hour.

The resulting catalyst in an amount of 10 cc was packed into a quartz tube having an inside diameter of 15 mm, and heated at 500°C. A gaseous mixture of 3-methyl-4-(p-tolyl) butane, benzene and nitrogen gas in a molar ratio of 1:3:8 was passed through this catalyst layer at normal atmospheric pressure. The contact time was 6.0 seconds.

The composition of the catalyst, the conversion of 3-methyl-4-(p-tolyl) butane, the selectivity of the dimethyl naphthalene mixture and the proportions of the isomers of the dimethyl naphthalene mixture are shown in Table 4.

EXAMPLE 16

Alumina having supported thereon potassium oxide and rhenium oxide which was prepared in the same way as in Example 14 was further immersed for several hours in an aqueous solution of chromium nitrate, dried, and calcined in an atmosphere of nitrogen at 700°C. for 3 hours. The composition of the resulting catalyst is shown in Table 4.

This catalyst in an amount of 10 cc was packed into a quartz tube being an inside diameter of 15 mm, and held at 500°C. Hydrogen gas was passed through the tube for one hour, and then in the same way as in Example 1, 3-methyl-4-(p-tolyl) butane was vaporized and passed through the tube.

Table 3

| Examples | 9 | 10 | 11 | 12 | 13 |
|---|---|---|---|---|---|
| Materials | 2-methyl-4-(p-tolyl)-2-butene and 2-methyl-4-(p-tolyl)-3-butene | 3-methyl-4-(p-tolyl)-2-butene | 3-methyl-4-(p-tolyl)-2-butene-3-methyl-4-(p-tolyl)-3-butene | 4-methyl-4-(p-tolyl)-2-butene and 4-methyl-4-(p-tolyl)-3-butene | 3-methyl-4-(p-tolyl)-butudiene |
| Conversion (%) | 91.2 | 90.2 | 89.5 | 85.4 | 72.0 |
| Selectivity of dimethyl naphthalene (%) | 78.4 | 79.0 | 78.5 | 76.8 | 35.2 |
| Proportions of the isomers of dimethyl naphthalene (%) | | | | | |
| 2,6-dimethyl naphthalene | 4.3 | 95.0 | 94.3 | 3.8 | 96.0 |
| 2,7-dimethyl naphthalene | 93.7 | 3.8 | 4.1 | 2.5 | 3.1 |
| 1,6-dimethyl naphthalene | 1.0 | 0.2 | 0.4 | 91.8 | 0.6 |
| 1,4-dimethyl naphthalene | trace | 0.4 | 0.8 | 0.5 | trace |
| 2,3-dimethyl naphthalene | trace | 0.4 | 0.5 | 0.3 | trace |
| Others | 1.0 | 0.2 | trace | 1.1 | 0.3 |

The composition of the catalyst, the conversion of 3-methyl-4-(p-tolyl) butane, the selectivity of the dimethyl naphthalene mixture, and the proportions of the isomers in the dimethyl naphthalene mixture are shown in Table 4.

Using this catalyst, 3-methyl-4-(p-tolyl) butane was cyclodehydrogenated under the same conditions as in Example 16. The results are shown in Table 4.

Table 4

| Examples | | 14 | 15 | 16 | 17 | 18 |
|---|---|---|---|---|---|---|
| Composition of the catalyst (wt %) | Rhenium oxide | 3.4 | 3.0 | 4.6 | 2.5 | 3.2 |
| | Alumina | 93.2 | 88.1 | 88.6 | 97.5 | 22.5 |
| | Silica | 0 | 0 | 0 | 0 | 72.6 |
| | Alkali or alkaline earth metal oxide | K* | Ca* | K* | | Na* |
| | | 3.4 | 8.9 | 3.4 | 0 | 1.7 |
| | Chromia | 0 | 0 | 3.4 | 0 | 0 |
| Conversion (%) | | 38.5 | 26.8 | 43.8 | 64.2 | 37.3 |
| Selectivity of dimethyl naphthalene (%) | | 68.6 | 79.2 | 67.3 | 43.5 | 64.5 |
| Proportions of the isomers of dimethyl naphthalene (%) | | | | | | |
| 2,6-dimethyl naphthalene | | 94.4 | 94.0 | 95.0 | 82.2 | 87.3 |
| 2,7-dimethyl naphthalene | | 4.0 | 3.3 | 2.2 | 8.7 | 6.5 |
| 1,6-dimethyl naphthalene | | 0.4 | 0.8 | 0.4 | 1.0 | 0.8 |
| 1,4-dimethyl naphthalene | | trace | trace | trace | 1.3 | 0.7 |
| 2,3-dimethyl naphthalene | | trace | trace | trace | 2.5 | 0.3 |
| Others | | 1.2 | 2.0 | 2.5 | 4.3 | 4.4 |

*K, Ca and Na respectively mean an oxide of potassium, an oxide of calcium and an oxide of sodium

EXAMPLE 17

Alumina as a carrier was pulverized to a particle size of not more than 100 mesh, and calcined at 700°C. While being sealed with a nitrogen gas the alumina was introduced into a glass filter connected to a flask containing commercially available rhenium heptoxide $Re_2O_7$. After reducing the pressure of the inside of the flask to below 10 mmHg, the flask was externally heated, and maintained at about 350°C. to sublime the rhenium heptoxide and cause it to adsorb to the alumina at the upper part of the filter.

Using the catalyst so prepared, 3-methyl-4-(p-tolyl) butane was cyclohydrogenated under the same conditions as in Example 16. The results are shown in Table 4.

EXAMPLE 18

Silica-alumina containing 25% of alumina was immersed for about 50 hours in a 5% by weight aqueous solution of sodium hydroxide, and calcined at 700°C. for 3 hours. Rhenium oxide was supported on the resulting sodium-poisoned silica-alumina by the method shown in Example 17.

EXAMPLE 19

Using the catalyst contained in Example 14, 2-methyl-4-(p-tolyl)-2-butene was cyclodehydrogenated under the same conditions as in Example 14. The results are shown in Table 5.

EXAMPLE 20

Using the catalyst obtained in Example 14, a mixture consisting of 25% of 3-methyl-4-(p-tolyl)-2-butene and 75% of 3-methyl-4-(p-tolyl)-3-butene was cyclodehydrogenated in the same way as in Example 14. The results are shown in Table 5.

EXAMPLE 21

Using the catalyst obtained in Example 14, 3-methyl-4-(p-tolyl) butadiene was cyclodehydrogenated under the same conditions as in Example 14 except that the reaction temperature was changed to 370°C. The results are shown in Table 5.

Table 5

| Example | 19 | 20 | 21 |
|---|---|---|---|
| Materials | 2-methyl-4-(p-tolyl)-2-butene | 3-methyl-4-(p-tolyl)-2-butene and 3-methyl-4-(p-tolyl)-3-butene | 3-methyl-4-(p-tolyl) butadiene |
| Conversion (%) | 91.0 | 72.0 | 57.0 |
| Selectivity of dimethyl naphthalene (%) | 80.0 | 83.5 | 42.2 |
| Proportions of the isomers of dimethyl naphthalene (%) | | | |
| 2,6-dimethyl naphthalene | 4.2 | 94.0 | 96.0 |
| 2,7-dimethyl naphthalene | 94.5 | 4.0 | 2.5 |
| 1,6-dimethyl naphthalene | 0.5 | 0.5 | 0.5 |
| 1,4-dimethyl naphthalene | 0.6 | 0.7 | 0.5 |
| 2,3-dimethyl naphthalene | trace | 0.4 | trace |
| Others | 0.2 | 0.3 | 0.3 |

EXAMPLE 22

3-Methyl-4-(p-tolyl) butane was cyclodehydrogenated under the same conditions as in Example 1 expect that toluene was used as a diluent instead of the benzene. The results are shown in Table 6.

EXAMPLE 23

3-Methyl-4-(p-tolyl) butane was cyclodehydrogenated under the same conditions as in Example 14 except that steam was used as a diluent instead of the nitrogen. The results are shown in Table 6.

EXAMPLE 24

5.4 g of commercially vaiIable ammonium perrhenate ($NH_4ReO_4$) and 40 g of chromium nitrate [$Cr(NO_3)_3 \cdot 9H_2O$] were pulverized and mixed in a mortar, and kneaded with a very small amount of water to form a paste-like mixture. The mixture was calcined in air at 450°C. for 2 hours. The catalyst so prepared consisted of 30% by weight of $Re_2O_7$ and 70% by weight of $CR_2O_3$.

7 g of this catalyst was packed in a reaction tube, and 3-methyl-4-(p-tolyl) butane was cyclodehydrogenated under the same conditions as in Example 3 except that the reaction temperature was changed to 400°C. The results are shown in Table 6.

Table 6

|  | Example 22 | Example 23 | Example 24 |
|---|---|---|---|
| Conversion (%) | 36.0 | 52.7 | 8.0 |
| Selectivity of dimethyl naphthalene (%) | 26.2 | 36.0 | 72.0 |
| Proportions of the isomers of dimethyl naphthalene (%) | | | |
| 2,6-dimethyl naphthalene | 70.5 | 96.0 | 96.2 |
| 2,7-dimethyl naphthalene | 12.5 | 3.3 | 3.1 |
| 1,6-dimethyl naphthalene | 2.6 | 0.4 | 0.6 |
| 1,4-dimethyl naphthalene | 0.8 | trace | trace |
| 2,3-dimethyl naphthalene | 5.0 | trace | trace |
| Others | 8.6 | 0.2 | 0.1 |

COMPARATIVE EXAMPLE 1

Example 1 was repeated except that a solid phosphoric acid catalyst consisting of 70% of o-phosphoric acid, 20% of diatomaceous earth and 10% of graphite was used, and the reaction temperature was changed to 350°C. The conversion of the starting 3-methyl-4-(p-tolyl) butane was 45%, and the resulting product consisted of 71% of dimethyl indane, 24% of 2,6-dimethyl tetralin and 3% of dimethyl naphthalene. Of the dimethyl naphthalenes obtained, 2,6-dimethyl naphthalene accounted for 70%.

COMPARATIVE EXAMPLE 2

Example 1 was repeated except that a Pt-C catalyst containing 0.05 by weight of platinum was used and the reaction temperature was changed to 500°C. The conversion of the starting 3-methyl-4-(p-tolyl) butane was 72%. The product consisted of 64% of toluene and xylene resulting from the dealkylation of the starting material, 23% of dimethyl indane, 5% of dimethyl naphthalene, and 8% of other matters. Of the dimethyl naphthalenes obtained, 2,6-dimethyl naphthalene accounted for 48%.

COMPARATIVE EXAMPLE 3

Example 1 was repeated except that a silica-alumina catalyst containing 25% of alumina same as used in Example 8 was used and the reaction temperature was changed to 500°C. The conversion of the 3-methyl-4-(p-tolyl) butane was 95%. The resulting product consisted of 90% of toluene and xylene resulting from the dealkylation of the starting material, 5% of dimethyl indane, 3% of dimethyl naphthalene, and 2% of other matters. Of the dimethyl naphthalenes obtained, 2,6-dimethyl naphthalene obtained accounted for 44%.

What is claimed is:

1. A process for preparing dimethyl naphthalenes selected from at least one of 1,6-, 2,6-, or 2,7-dimethyl naphthalene which comprises heating a compound (I) selected from the group consisting of methyl-4-(p-tolyl)butane, methyl-4-(p-tolyl) butene and methyl-4-(p-tolyl)butadiene wherein the p-tolyl is attached at the terminal position of the butane, butene or butadiene skeleton, in the vapor phase at a temperature of about 200°C to about 700°C for a contact time of about 0.1 to about 15 seconds, in the presence of the cyclization-dehydrogenation catalyst selected from the group consisting of (a) an oxide of rhenium and (b) a mixture of (a) with an oxide of chromium.

2. The process of claim 1 wherein the amount of the catalyst is about 0.001 mol to about 1 mol per mol of the compound (I).

3. The process of claim 1 wherein the catalyst is supported on a solid carrier and further contains an oxide of a metal selected from the group consisting of alkali metals and alkaline earth metals.

4. The process of claim 3 wherein the amount of said alkali or alkaline earth metal oxide is 0.1 to 20% by weight based on the weight of the catalyst.

5. The process of claim 3 wherein the amount of said metal oxide is 0.5 to 10% by weight calculated as metal based on the weight of the solid carrier.

6. The process of claim 1 wherein the compound (I) is a compound obtained by the addition reaction of p-xylene with a compound selected from the group consisting of butene and butadiene.

7. The process of claim 1 wherein said dimethyl naphthalene is selected from at least one of 2,6- or 2,7-dimethyl naphthalene and said compound (I) is selected from the group consisting of 2-methyl-4-(p-tolyl)butane and 3-methyl-4-(p-tolyl)butane.

8. The process of claim 7 wherein the amount of said catalyst is about 0.001 mol to about 1 mol per mole of the compound (I).

9. The process of claim 7 wherein said catalyst further contains an oxide of a metal selected from the group consisting of alkali metals and alkaline earth metals.

10. The process of claim 9 wherein the amount of said alkalo alkali alkaline earth metal oxide is 0.1 to 20% by weight based on the weight of the catalyst.

11. The process of claim 9 wherein the amount of said metal oxide is 0.5 to 10% by weight calculated as metal based on the weight of the solid carrier.

12. The process of claim 1 wherein said catalyst is an oxide of rhenium.

13. The process of claim 7 wherein said catalyst is an oxide of rhenium.

* * * * *

UNITED STATES PATENT OFFICE
CERTIFICATE OF CORRECTION

Patent No. 3,931,348          Dated January 6, 1976

Inventor(s) TANIGUCHI, ET AL.

It is certified that error appears in the above-identified patent and that said Letters Patent are hereby corrected as shown below:

Item 30, line 3, delete "Feb. 14, 1973", insert
-- Feb. 16, 1973 --

Claim 10, line 2, delete "alkalo alkali", insert -- alkali or --

Signed and Sealed this thirtieth Day of March 1976

[SEAL]

Attest:

RUTH C. MASON
Attesting Officer

C. MARSHALL DANN
Commissioner of Patents and Trademarks